United States Patent [19]

Harandi

[11] Patent Number: 5,004,852
[45] Date of Patent: Apr. 2, 1991

[54] TWO-STAGE PROCESS FOR CONVERSION OF OLEFINS TO HIGH OCTANE GASOLINE

[75] Inventor: Mohsen N. Harandi, Lawrenceville, N.J.

[73] Assignee: Mobil Oil Corp., Fairfax, Va.

[21] Appl. No.: 399,182

[22] Filed: Aug. 24, 1989

[51] Int. Cl.$^5$ .......................... C07C 2/12; C07C 15/02
[52] U.S. Cl. .................................. 585/322; 585/407; 585/415; 585/522
[58] Field of Search ................ 585/322, 407, 415, 522

[56] References Cited

U.S. PATENT DOCUMENTS

| | | | |
|---|---|---|---|
| 3,827,968 | 8/1974 | Givens et al. | 208/49 |
| 3,845,150 | 10/1974 | Yan et al. | 260/673.5 |
| 3,960,978 | 6/1976 | Givens et al. | 260/683.15 R |
| 4,021,502 | 5/1977 | Plank et al. | 260/683.15 R |
| 4,150,062 | 4/1979 | Garwood et al. | 260/673 |
| 4,211,640 | 7/1980 | Garwood et al. | 208/255 |
| 4,227,992 | 10/1980 | Garwood et al. | 208/46 |
| 4,433,185 | 2/1984 | Tabak | 585/312 |
| 4,456,779 | 6/1984 | Owen et al. | 585/415 |
| 4,497,968 | 2/1985 | Wright et al. | 585/304 |

*Primary Examiner*—Curtis R. Davis
*Attorney, Agent, or Firm*—Alexander J. McKillop; Charles J. Speciale; Robert B. Furr, Jr.

[57] ABSTRACT

Light aliphatic streams containing $C_4-$ olefins are upgraded to $C_5+$ gasoline in a two-stage process. In the first stage, olefins are oligomerized to $C_5+$ olefinic gasoline. Unreacted light aliphatics including ethylene as well as light oligomerization byproducts are then charged to a second stage aromatization zone. Catalysts useful for both stages include medium pore zeolites.

10 Claims, 3 Drawing Sheets

TWO-STAGE PROCESS FOR CONVERSION OF OLEFINS TO HIGH OCTANE GASOLINE

BACKGROUND OF THE INVENTION

This invention relates to a catalytic technique for upgrading olefin streams to gasoline streams rich in aromatics. In particular, it provides a continuous process for oligomerizing and aromatizing a feedstock containing light $C_4-$ olefins to produce $C_5+$ hydrocarbons rich in $C_6-C_{10}$ aromatics, such as benzene, toluene, xylenes, tri- and tetramethylbenzenes together with hydrogen and fuel gas.

Developments in zeolite catalysis and hydrocarbon conversion processes have created interest in utilizing olefinic feedstocks for producing $C_5+$ gasoline, distillate and lubricants. In addition to the basic chemical reactions promoted by medium-pore zeolite catalysts, a number of discoveries have contributed to the development of new industrial processes. These are safe, environmentally acceptable processes for utilizing feedstocks that contain olefins. Conversion of $C_2-C_4$ alkenes and alkanes to produce aromatics-rich liquid hydrocarbon products were found by Cattanach (U.S. Pat. No. 3,760,024) and Yan et al. (U.S. Pat. No. 3,845,150) to be effective in the presence of a medium-pore zeolite catalysts. In U.S. Pat. Nos. 3,960,978 and 4,021,502, Plank, Rosinski and Givens disclosed conversion of $C_2-C_5$ olefins, alone or in admixture with paraffinic components, into higher hydrocarbons over crystalline zeolites having controlled acidity. Garwood et al. have also contributed to the understanding of catalytic olefin upgrading techniques and improved processes as in U.S. Pat. Nos. 4,150,062; 4,211,640 and 4,227,992. The above-identified disclosures are incorporated by reference as if set forth at length herein.

Conversion of olefins is effective in the presence of medium-pore zeolite catalysts at moderately elevated temperatures and pressures. The conversation products are sought as liquid fuels, especially the $C_5+$ aliphatic and aromatic hydrocarbons. Product distribution for liquid hydrocarbons can be varied by controlling process conditions, such as temperature, pressure and space velocity. Aromatic gasoline ($C_5-C_{10}$) is readily formed at elevated temperature (e.g., about 420° to 650° C.) and moderate pressure from ambient to about 5500 kPa, preferably about 200 to 2900 kPa. Olefinic gasoline can also be produced and may be recovered as a product or may be further upgraded to aromatic gasoline in a high severity reactor system. Alternatively, the olefinic gasoline may be charged to a low severity, high pressure reactor system for further conversion to heavier distillate range products. Operating details for typical "MOGD" oligomerization units are disclosed in U.S. Pat. Nos. 4,150,062 to Garwood et al.; 4,456,779 and 4,497,968 to Owen et al., as well as 4,433,185 to Tabak, which patents are incorporated herein by reference.

U.S. Pat. No. 3,827,968 to Givens et al. teaches a two-step process for aromatization of aliphatics. The first step comprises olefin oligomerization in the presence of a medium-pore zeolite catalyst. Oligomerized liquid product is then separated from oligomerization reactor effluent and charged to an aromatization stage. Both stages are operated in the absence of added hydrogen. The '968 patent expressly states that the second stage aromatization process is made considerably more efficient by having its feed limited to the liquid phase product of the first stage oligomerization.

With the ever-increasing demand for high octane unleaded gasoline, it would be advantageous to provide a two-stage aliphatics upgrading process which yields an increased volume of gasoline at the expense of less valuable $C_4-$ aliphatics.

SUMMARY OF THE INVENTION

A new method has been found for two-stage olefin conversation employing a first gasoline mode oligomerization reaction zone and second aromatization reaction zone. Advantageously, the pressure differential between the two stages can be utilized in an intermediate flashing separation step. Unreacted ethylene and other light gases are readily recovered from heavier hydrocarbons in the flashing step and these light hydrocarbon gases are then aromatized in a downstream reaction zone.

Thus, the process produces two gasoline streams. The first stream, oligomerized gasoline rich $C_5+$ olefins, is produced in the first, or oligomerization, reaction zone under relatively mild conditions of temperature, pressure and space velocity. The total oligomerization reaction zone effluent may be charged to an aromatization zone. However, the oligomerization reaction zone effluent is preferably fractionated into a $C_4-$ aliphatic stream and a $C_5+$ olefinic gasoline stream, and the $C_4-$ aliphatic stream is aromatized while the $C_5+$ olefinic gasoline is routed to product blending or storage.

Accordingly, it is an object of this invention to provide a continuous system for converting a feedstock containing ethylene and $C_3+$ olefins by catalytic oligomerization to produce olefinic and aromatic gasoline in a first catalytic reaction zone and aromatizing the resulting $C_4-$ light aliphatic gas stream in a second catalytic aromatization zone which comprises the steps of (a) contacting the olefinic feedstock in a first catalytic reaction zone with a crystalline zeolite oligomerization catalyst at elevated pressure and moderate temperature under conditions favorable for conversion of $C_3+$ olefins to a first reaction zone effluent stream rich in gasoline range hydrocarbons; (b) flashing the first reaction-zone effluent stream and to separate the first reaction zone effluent stream into a liquid stream rich in $C_5+$ olefinic and aromatic gasoline and a vapor stream rich in $C_4-$ aliphatics including ethylene, and (c) contacting the vapor stream from step (b) in a second catalytic reaction zone with a crystalline zeolite aromatization catalyst at moderate pressure and elevated temperature under conditions favorable for conversion of ethylene and light $C_4-$ aliphatics to a second reaction zone effluent stream rich in aromatic gasoline.

DETAILED DESCRIPTION

Conversion of olefins to gasoline is disclosed, for example, in U.S. Pat. Nos. 3,960,978 and 4,021,502 to Givens, Plank and Rosinski. These processes convert gaseous olefins in the range of ethylene to pentene, either along or in admixture with paraffins into an olefinic gasoline blending stock by contacting the olefins with a catalyst bed made up of a medium-pore zeolite. Medium pore zeolite catalysts are exemplified in these processes by zeolites having the structure of ZSM-5. In U.S. Pat. No. 4,227,992, Garwood and Lee disclose the operating conditions for the Mobil Olefin to Gasoline Distillate (MOGD) process for selective conversion of $C_{3+}$ olefins and only 20% maximum ethylene conversion. Similarly, U.S. Pat. No. 4,150,062 to Garwood et al. discloses a process for converting olefins to gasoline compounds. The MOGD process typically recycles cooled gas or liquid $C_3$–$C_4$ alkanes from a high-temperature, high-pressure separator downstream of the catalyst bed back into the reaction zone where additional olefins are converted to gasoline and distillate products. If the conversion of olefins to gasoline and distillate is allowed to progress in the catalyst stream without heat removal, the reaction accelerates exothermically and produces undesired products.

The first stage reaction zone of the present process converts light olefins under oligomerization conditions as shown in Table 1, below.

TABLE 1

Medium-Pore Zeolite Catalyzed Conversion of Light $C_4$ - Olefins to Gasoline

| WHSV | Broad | $0.1$–$50$ $hr^{-1}$ |
| --- | --- | --- |
|  | Preferred | $0.5$–$10$ $hr^{-1}$ |
| Reaction | Broad | 170–510° C. (350–950° F.) |
| Zone | Preferred | 200–320° C. (400–600° F. |
| Temperature |  |  |
| Reaction | Broad | 240–2900 kPa (20–400 psig) |
| Zone | Preferred | 790–1500 kPa (100–200 psig) |
| Pressure |  |  |

The second stage reaction zone of the present process converts light aliphatics including ethylene to $C_{5+}$ aromatics under aromatization conditions shown in Table 2, below:

TABLE 2

Medium-Pore Zeolite Catalyzed Aromatization of Light $C_4$ - Aliphatics

| WHSV | Broad | $0.3$–$300$ $hr^{-1}$ |
| --- | --- | --- |
|  | Preferred | $1$–$10$ $hr^{-1}$ |
| Reaction | Broad | 510–820° C. (950–1500° F.) |
| Zone | Preferred | 530–600° C. (1000–1100° F.) |
| Temperature |  |  |
| Reaction | Broad | 100–2500 kPa (0–350 psig) |
| Zone | Preferred | 170–1500 kPa (10–200 psig) |
| Pressure |  |  |

Figure 1:
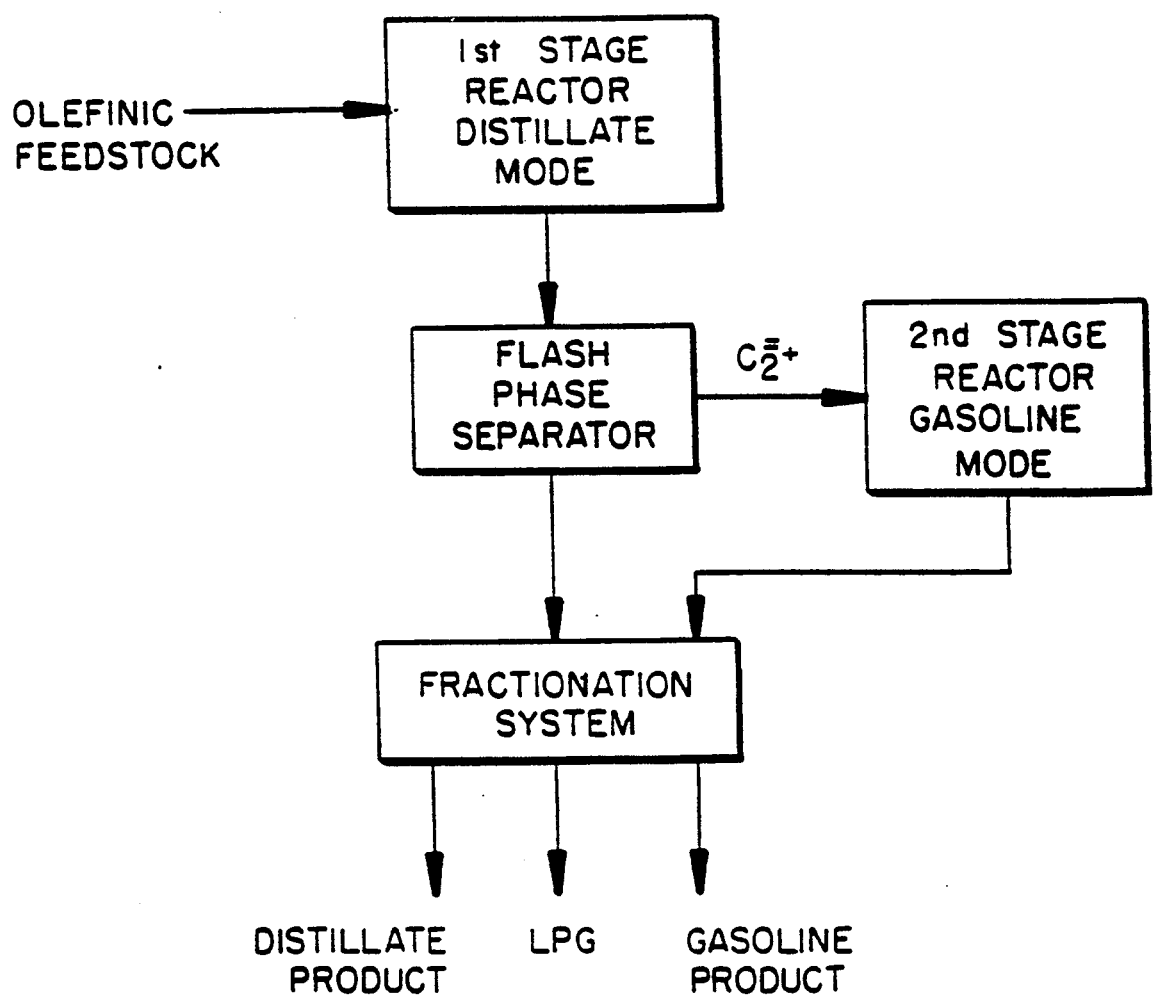
FIG. 1 is a process flow diagram showing unit operations and hydrocarbon streams.

In FIG. 1 the conceptual design is shown in block process flow diagram form, with the olefinic feedstock comprising ethylene toegether with $C_3$–$C_6$ olefins is passed to the first stage reaction zone operating at high pressure in a maximum gasoline production mode. The first stage effluent is cooled and reduced in pressure by flashing into a phase separation zone to provide an ethylene-rich vapor phase and a gasoline-rich liquid hydrocarbon phase. This separation unit is preferably operated to recover a major amount of $C_{5+}$ hydrocarbons and to pass the unconverted $C_{4-}$ aliphatic gases to the downstream aromatization zone. The unreacted ethylene and other light gases are then catalytically reacted at elevated temperature and moderate pressure to form addition $C_{6+}$ hydrocarbons rich in aromatic gasoline. Effluent from each reaction zone may be fractionated separately or combined in an interconvated fractionation system as shown to recover the desired products. A portion of the $C_{4-}$ alkanes (LPG) may be recycled to dilute the ethylene rich second stage feedstream to provide heat balanced operation in the second stage aromatization reactor. This system is adapted for intergrating a first MOG reaction zone with a second M-2 forming (aromatization) reaction zone, which reaction zones are operating at different reaction conditions to maximize gasoline production from a light $C_{4-}$ olefinic stream.

ZEOLITE CATALYSTS

The members of the class of zeolites useful in the oligomerization and aromatization reactions of the present process have an effective pore size of generally from about 5 to about 8 Angstroms, such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules are larger cross section than normal hexane is excluded and the zeolite is not of the desired type. Windows of 10-membered rings are preferred, although, in some instances, excessive puckering of the rings or pore blockage may render these zeolites ineffective.

Although 12-membered rings in theory would not offer sufficient constraint to produce advantageous conversions, it is noted that the puckered 12-ring structure of TMS offretite does show some constrained access. Other 12-ring structures may exist which may be operative for other reasons, and therefore, it is not the present intention to entirely judge the usefulness of the particular zeolite solely from theoretical structural considerations.

A convenient measure of the extent to which a zeolite provides control to molecules of varying sizes to its internal structure is the Constraint Index of the zeolite. The method by which the Constraint Index is determined is described in U.S. Pat. No. 4,016,218, incorporated herein by reference for details of the method. U.S. Pat. No.4,696,732 discloses Constraint Index values for typical zeolite materials and is incorporated by reference as if set forth at length herein.

In a preferred embodiment, the catalyst is a zeolite having a Constraint Index of between about 1 and about 12. Examples of such zeolite catalysts include ZSM-5, ZSM-11, ZSM-22, ZSM-23, ZSM-35 and ZSM-48.

Zeolite ZSM-5 and the conventional preparation thereof are described in U.S. Pat. No. 3,702,886, the disclosure of which is incorporated herein by reference. Other preparations for ZSM-5 are described in U.S. Pat. Nos. Re. 29,948 (highly siliceous ZSM-5); 4,100,262 and 4,139,600, the disclosure of these is incorporated herein by reference. Zeolite ZSM-11 and the conventional preparation thereof are described in U.S. Pat. No. 3,709,979, the disclosure of which is incorporated herein by reference. Zeolite ZSM-12 and the conventional preparation thereof are described in U.S. Pat. No. 3,832,449, the disclosure of which is incorporated herein by reference. Zeolite ZSM-23 and the conventional preparation thereof are described in U.S. Pat. No. 4,076,842, the disclosure of which is incorporated herein by reference. Zeolite ZSM-35 and the conventional preparation thereof are described in U.S. Pat. No. 4,016,245, the disclosure of which is incorporated herein by reference. Another preparation of ZSM-35 is described in U.S. Pat. No. 4,107,195, the disclosure of which is incorporated herein by reference. ZSM-48 and the conventional preparation thereof is taught by U.S. Pat. No. 4,375,573, the disclosure of which is incorporated herein by reference.

Galium-containing zeolite catalysts are particularly preferred for use in the present invention and are disclosed in U.S. Pat. No. 4,350,835 and U.S. Pat. No. 4,686,312, both of which are incorporated by reference as if set forth in length herein.

Zinc-containing zeolite catalysts are useful in the present invention, for example, U.S. Pat. No. 4,392,989 and U.S. Pat. No. 4,472,535, both of which are incorporated by reference as if set forth at length herein.

Catalysts such as ZSM-5 combined with a Group VIII metal described in U.S. Pat. No. 3,856,872, incorporated by reference as if set forth at length herein, are also useful in the present invention.

FEEDSTREAMS

To fully realize the advantages of the present inventive process, the preferred feedstock to be charged to the first stage of the intergrated system should contain at least 5 mole % ethylene, preferably 10 50%, and substantially no hydrogen. A typical olefinic feedstock contains a major fraction (50+ mole %) of combined $C_2$-$C_4$ alkenes with minor amounts of $C_5+$ alkenes. Other volatile hydrocarbons such as low molecular weight paraffins are often found in many petroleum refinerby streams, such as catalytic cracker by-product depropanizer off-gas. The most preferred source for such an olefin-rich feedstream is the unsaturate gas plant (product fractionation section) of a fluid catalytic cracking unit. It is an object of the present invention to upgrade lower olefinic hydrocarbons to more valuable liquid fuel products rich in $C_5+$ olefinic and aromatic gasoline.

PROCESS FLOW

Figure 2:
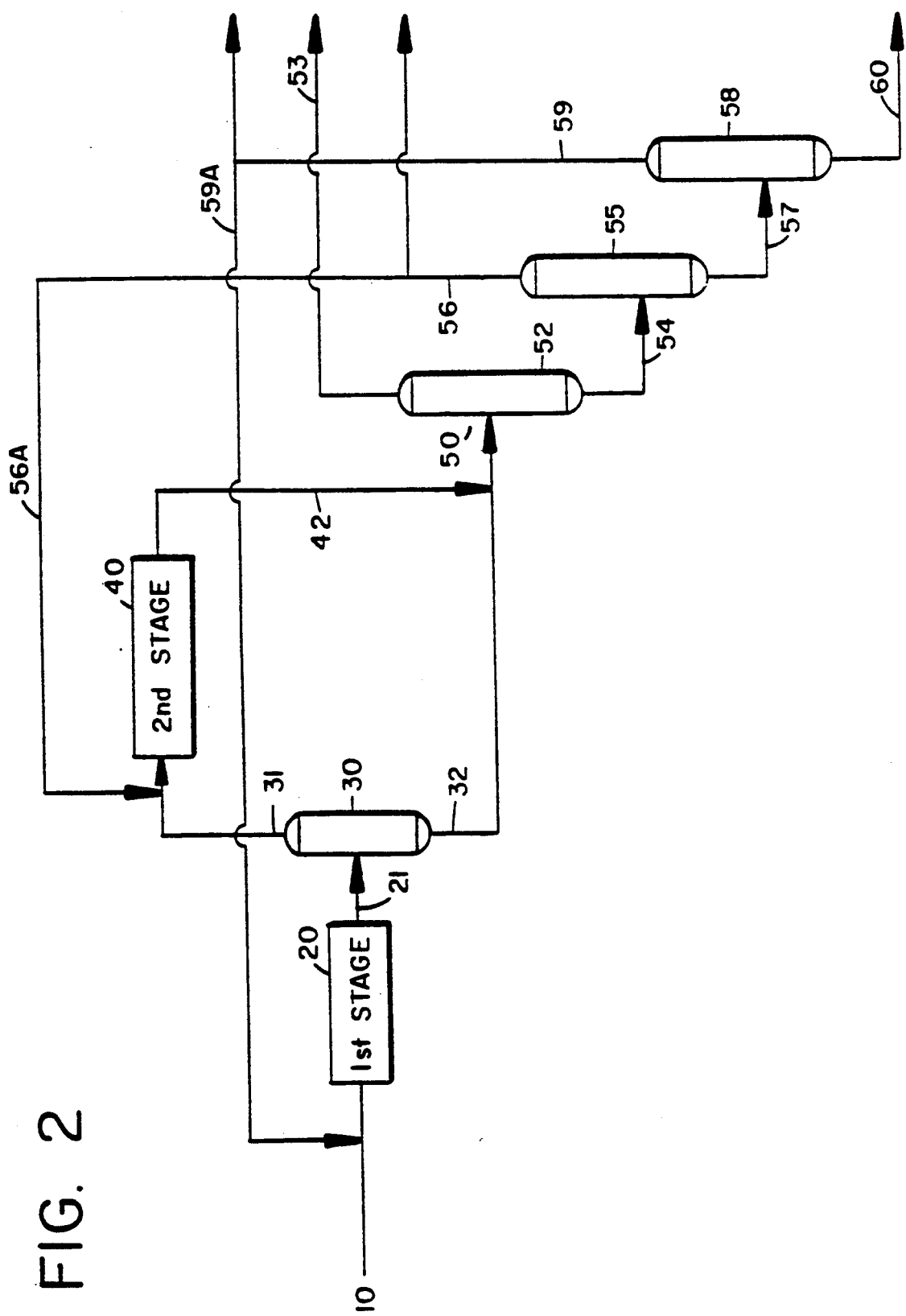
FIG. 2 is a simplified schematic diagram of a preferred two-stage reactor system and a multi-tower fractionation system.

Referring to the drawing of FIG. 2, the flow sheet shows a preferred process wherein the total olefinic feedstock 10 is charged to a gasoline mode first stage reaction zone 20. Here the $C_3+$ olefins are readily converted to olefinic and aromatic gasoline, while the extent of $C_2-$ reaction is low, on the order of 10 20%. The reactor effluent is then flashed in separator 30 to give a pressurized vapor phase (primarily $C_5-$), which is cascaded at a lower pressure through line 31 to an aromatization reaction zone 40. The liquid component of the first stage reaction zone effluent is then charged through line 32 to fractionator 50 together with the second stage reaction zone effluent flowing through line 42.

A series of fractionation towers includes deethanizer column 52 from which $C_1$-$C_2$ off-gas is withdrawn as overhead vapor stream 53. Heavier components in bottom stream 54 are further fractionated in debutanizer column 55 to provide $C_3$-$C_4$ overhead stream 56. This stream may be recovered as LPG product and/or recycled to the aromatization reaction zone 40 via line 56A to help control the heat of reaction. Heat-balanced aromatization of light aliphatic hydrocarbons is taught in U.S. Pat. No. 3,845,150 to Yan and Zahner, which patent is incorporated herein by reference for the details of such heat balanced operation. Debutanizer bottom stream 57 is sent to product storage or to a gasoline treatment facility for blending into saleable product.

Figure 3:
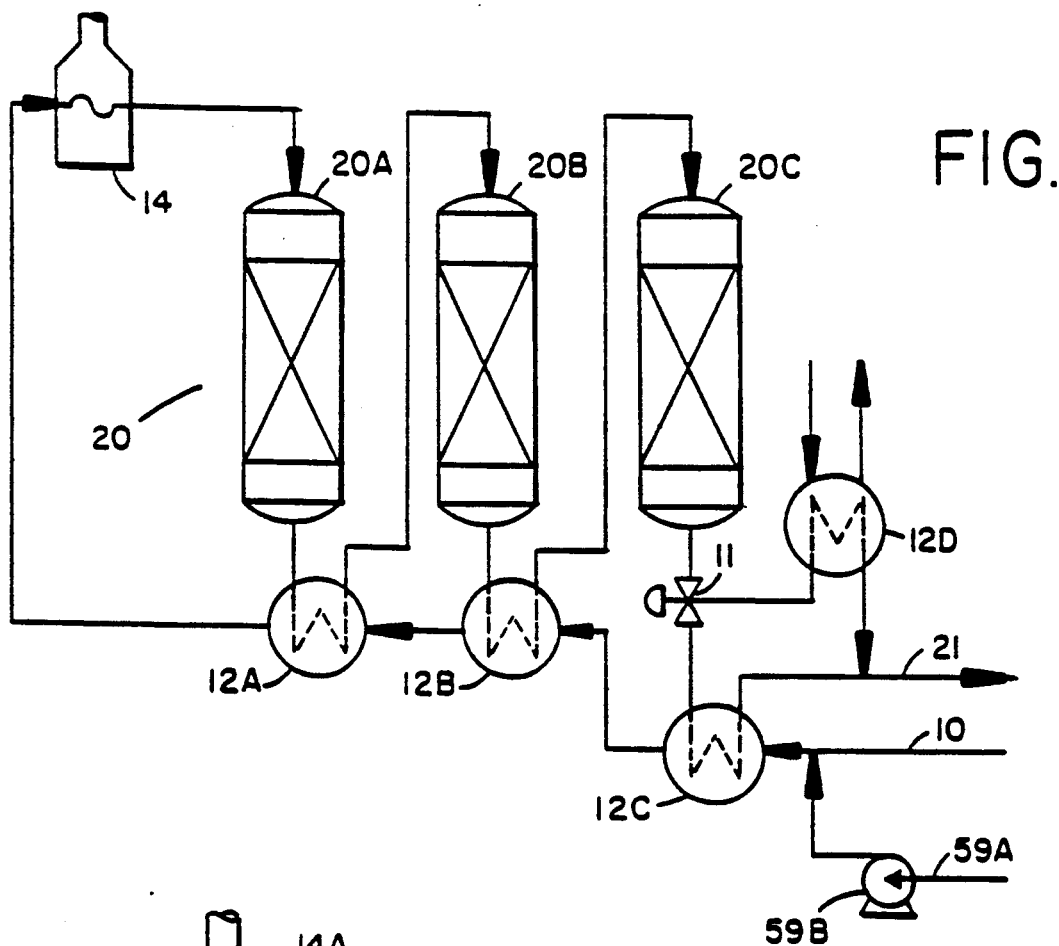
FIG. 3 is a typical olefin conversion reactor system for first stage gasoline mode operation.

A typical gasoline mode first stage reactor system 20 is shown in FIG. 3. A multi-reactor system is employed with inter-zone cooling, whereby the reaction exotherm can be carefully controlled to prevent excessive temperatures above normal moderate range of about 170° to 380° C. (350° to 750° F.). $C_2$-$C_6$ olefinic feedstock is introduced through conduit 10 and carried by a series of conduits through heat exchangers 12A, 12B and 12C, and furnace 14 where the feedstock is heated to reaction temperature. The olefinic feedstock is then carried sequentially through a series of catalyst beds 20A, 20B and 20C, wherein at least a portion of the olefin content is converted to olefinic and aromatic gasoline constituents. Advantageously, the maximum temperature differential across only one reactor is about 30° C. (about 50° F.) and the space velocity (WHSV based on olefin feed) is about 0.5 to 10 hr.$^{-1}$. The heat exchangers 12A and 12B provide inter-reactor coolant and 12C reduces the effluent to flashing temperature. An optional heat exchanger 12D may further recover heat from the effluent stream 21 prior to phase separation. Gasoline from recycle conduit 59A is pressurized by pump 59B and combined with feedstock, preferably at a ratio of about 1-3 parts by weight per part of olefin in the feedstock.

Between stages it is preferred to take advatage of the pressure drop by flashing the effluent with a pressure differential of at least 135 kPa (20 psi) between the first stage and phase separator vessel 30. By operating the first stage at a pressure of about 790 to 1500 kPa (100 to 200 psig), this can be achieved. Any suitable enclosed pressure vessel can be used as the separator unit, which is operatively connected by conduits 21, 31 and 32 in fluid flow relationship to the two stages and fractionation system. This configuration is described above with reference to FIG. 2.

Figure 4:
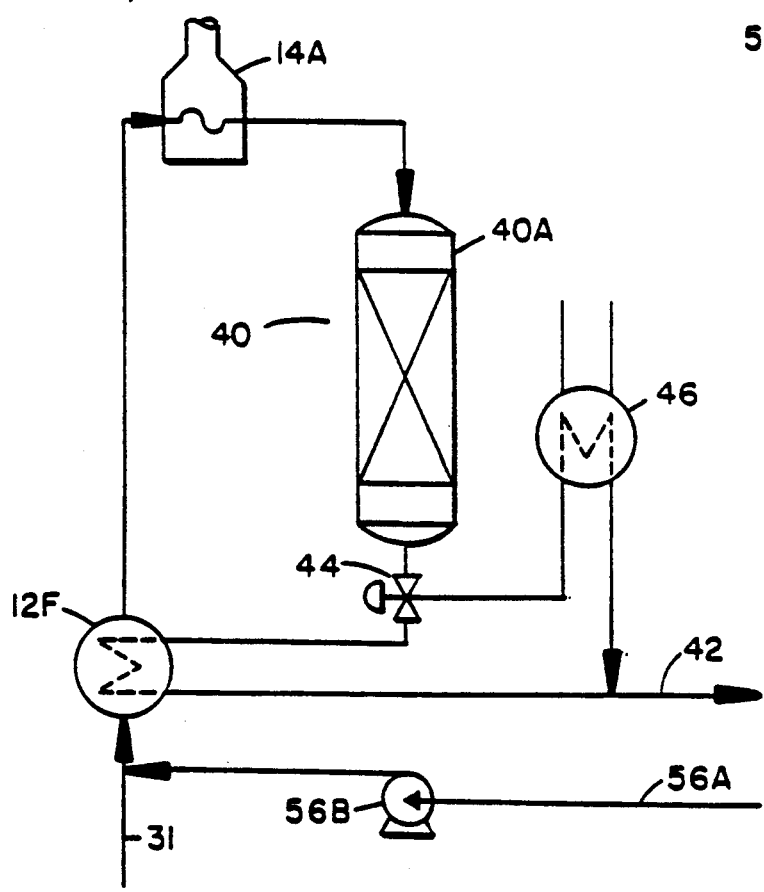
FIG. 4 is a typical second stage reactor system for aromatization of light $C_4-$ aliphatics to gasoline.

The aromatization reactor 40 shown in FIG. 4 is relatively simple, since the higher temperature conversion does not require maximum differential temperature control closer than about 65° C. (120° F.) in the approximate elevated range of 510° to 820° C. n950°-1500° F.). The reactor bed 40A is maintained at a pressure of about 170 to 1500 kPa (10 to 200 psig) and the weight hourly space velocity to optimize aromatic gasoline production should preferably fall within the range of about 1 to 10 hr.$^{-1}$.

Most of the pressure drop across the reactor system is taken prior to entering the flashing vessel 30 such that the flashing vessel is maintained at a pressure only high enough to allow overhead vapor to cascade into the aromatization reactor 40. Uncoverted ethylene and other light gases are passed from the separator through conduit 31, heat exchanger 12F, and furnace 14A to aromatization reactor bed 40A. The second stage effluent is cooled partially and exchanger 12F which partially preheats the reactor feed. The second stage reactor effluent then passes through conduit 42 to the fractionation system 50. Optionally, a portion of the hot effluent may be diverted by valve 44 through heat recovery exchanger 46. $C_3$-$C_4$ alkanes or other diluents may be introduced through recycle conduit 56A and pump 56B.

The process of the present invention has been described in terms of its application to fixed catalyst bed reactors. However, it is to be understood that the present process may also be carried out using one or more moving-bed or fluid bed reactors, or a combination of two or more fixed, moving or fluid bed reactors.

COMPUTER-SIMULATED EXAMPLES

The following computer simulated test runs illustrate the beneficial yield and selectivity improvements associated with the present inventive process. Each simulated test is based on a feedstream having a composition and mass flowrate as shown below in Table 3.

TABLE 3

| Feed Rate and Composition | | |
|---|---|---|
|  | Lbs/Hr. | Wt. % |
| $H_2$ | — | — |
| $C_1$ | — | — |
| $C_2=$ | 58.0 | 0.15 |
| $C_2$ | 566.1 | 1.42 |
| $C_3=$ | 14356.4 | 35.94 |
| $C_3$ | 3486.1 | 8.73 |
| $C_4$'s | 12513.2 | 31.33 |
| $C_4$'s | 8963.3 | 22.44 |
| $C_5+$ | — | — |
| Total | 39943.1 | 100.01 |

COMPARATIVE EXAMPLE NO. 1

Example No. 1 shows a typical product distribution for a two-stage process for producing gasoline from a $C_4$—aliphatic feedstream. In the first stage, the $C_4$—feedstream shown in Table 1 is contacted with a medium-pore zelite catalyst under conversion conditions shown below in Table 4.

TABLE 4

| WHSV | 1.0 hr$^{-1}$ |
|---|---|
| TEMPERATURE | 316° C. (600° F.) |
| PRESSURE | 1000 kPa (130 psig) |
| CATALYST | H-ZSM-5 |

The first stage effluent is then fractionated into $C_4$—overhead stream and a $C_5+$bottom stream. The $C_5+$bottom stream is contacted with a medium-pore zeolite catalyst under conversion conditions shown below in Table 5.

TABLE 5

| WHSV | 0.5 hr$^{-1}$ |
|---|---|
| TEMPERATURE | 594° C. (1000° F.) |
| PRESSURE | 170 kPa (10 psig) |

The total product yields for computer-simulated Comparative Example No. 1 are shown in Table 6, below:

TABLE 6

| Product Rate and Composition | | |
|---|---|---|
|  | Lbs/Hr. | Wt. % |
| $H_2$ | 1287.4 | 3.22 |
| $C_2-$ | 6842.1 | 17.13 |
| $C_3$-$C_4$ | 18725.0 | 46.88 |
| $C_5+$ | 13088.3 | 32.77 |
| Total | 39943.1 | 100.00 |
| $C_5+$ Gasoline Octane (R + O) | 113 |  |

EXAMPLE NO. 2

Example No. 2 illustrates the beneficial improvement in $C_5+$gasoline yield shown for computer simulation of a two-stage process for converting $C_4-$ aliphatics of the present invention.

The $C_4-$aliphatic feedstream of Table 3 is contacted with a medium-pore zeolite catalyst under conversion conditions shown above in Table 4. The first stage effluent is then contacted with a medium-pore zeolite catalyst under conversion conditions shown above in Table 5.

Table 7 shows the beneficial shift in selectivity to produce 84 weight percent more $C_5+$gasoline than the process of Comparative Example 1.

TABLE 7

| Product Rate and Composition | | |
|---|---|---|
|  | Lbs./Hr. | Weight % |
| $H_2$ | 2362.5 | 5.91 |
| $C_2-$ | 11985.5 | 30.01 |
| $C_3$-$C_4$ | 1575.0 | 3.94 |
| $C_5+$ | 24020.0 | 60.14 |
| Total | 39943.1 | 100.00 |
| $C_5+$ Gasoline Octane (R + O) | 113 |  |

EXAMPLE NO. 3

Example No. 3 shows the most preferred embodiment of the present invention. $C_5+$gasoline yield is markedly improved in this computer simulated example by contacting the feedstream of Table 3 in a first stage with a medium-pore zeolite under the process conditions of Table 4, above. The first stage effluent is then fractionated into a $C_4-$ overhead stream and a $C_5+$bottom stream. Unlike comparative Example No. 1 which further upgrades the bottom stream, the most preferred embodiment of the present invention contacts the $C_4+$ overhead with a medium-pore zeolite catalyst under the conversion conditions of Table 5. The total product yields are shown below in Table 8.

TABLE 8

| Product Rate and Composition | | |
|---|---|---|
|  | Lbs./Hr. | Weight % |
| $H_2$ | 1075.2 | 2.69 |
| $C_2-$ | 5763.1 | 14.43 |
| $C_3$-$C_4$ | 716.8 | 1.79 |
| $C_5+$ | 32388.0 | 81.09 |
| Total | 39943.1 | 100.00 |
| $C_5+$ Gasoline Octane (R + O) | 100 |  |

Changes and modifications in the specifically described embodiments can be carried out without departing from the scope of the invention which is intended to be limited only by the scope of the appended claims.

What is claimed is:

1. A continuous process for converting an olefinic feedstock containing ethylene and $C_3+$olefins by catalytic oligomerization and aromatization to produce high octane gasoline which comprises the steps of:
   (a) contacting the olefinic feedstock in a first catalytic oligomerization zone with a crystalline zeolite oligomerization catalyst at pressure of about 240 to 2900 kPa (20 to 400 psig), temperature of about 170° to 510° C. and WHSV of about 0.1 to about 50 hr$^{-1}$ to convert $C_3+$olefins to a first reaction zone effluent stream rich in oligomerized gasoline range hydrocarbons;
   (b) flashing the first reaction zone effluent stream to separate said first reaction zone effluent stream into a liquid stream rich in $C_5+$ gasoline and a vapor stream rich in ethylene; and (c) contacting the vapor stream from step (b) in a second catalytic reaction zone with a crystalline zeolite aromatization catalyst to pressure of about 150 to 1500 kPa (10 to 200 psig), temperature of about 510° to 820° C. (950° to 1500° F.) and WHSV of about 0.3 to 300 hr$^{-1}$ to convert ethylene and other lower olefins to a second reactor effluent stream rich in aromatic gasoline.

2. The process of claim 1 wherein second reactor effluent stream is fractionated to provide a $C_3$-$C^4$ rich stream for recycle to the second reaction zone.

3. The process of claim 1 wherein said zeolites each have a Constraint Index of between about 1 and about 12.

4. The process of claim 3 wherein said zeolites have the structure of at least one selected from the group consisting of ZSM-5, ZSM-11, ZSM-22, ZSM-23, ZSM-35 and ZSM-48.

5. The process of claim 4 wherein at least one zeolite has the structure of ZSM-5.

6. The process of claim 4 wherein said zeolite contains gallium.

7. The process of claim 4 wherein said catalytic reaction zones comprise fixed bed downflow pressurized reactors having porous beds of zeolite catalyst particles.

8. The process of claim 4 wherein at least one catalytic reaction zone comprises a fluid bed.

9. The process of claim 4 wherein said first catalytic oligomerization zone is maintained at a pressure of about 790 to 1500 kPa (100 to 200 psig), temperature of about 200° to 320° C. and WHSV of about 0.5 to 10 hr$^{-1}$.

10. The process of claim 4 wherein said second catalytic aromatization zone is maintained at a pressure of about 170 to 1500 kPa (10 to 200 psig), temperature of about 530° to 600° C. (1000° to 1100° F.) and WHSV of about 1 to 10 hr$^{-1}$.

* * * * *